United States Patent
Oroskar et al.

(10) Patent No.: US 9,452,968 B1
(45) Date of Patent: Sep. 27, 2016

(54) SEPARATION OF ADIPIC ACID AND DODECANEDIOIC ACID FROM CORRESPONDING MONOACID AND HYDROXY ACID

(71) Applicant: OROCHEM Technologies, Inc., Naperville, IL (US)

(72) Inventors: Anil R. Oroskar, Oak Brook, IL (US); Anantha Krishna Mallia, Rockford, IL (US)

(73) Assignee: OROCHEM TECHNOLOGIES, Inc., Naperville, IL (US)

( * ) Notice: Subject to any disclaimer, the term of this patent is extended or adjusted under 35 U.S.C. 154(b) by 21 days.

(21) Appl. No.: 14/693,445

(22) Filed: Apr. 22, 2015

(51) Int. Cl.
  *C07C 59/185* (2006.01)
  *C07C 51/47* (2006.01)
(52) U.S. Cl.
  CPC ...................... *C07C 51/47* (2013.01)
(58) Field of Classification Search
  CPC ....................................................... C07C 51/47
  USPC ......................................................... 554/121
  See application file for complete search history.

(56) References Cited

U.S. PATENT DOCUMENTS

| | | |
|---|---|---|
| 2,985,589 A | 5/1961 | Broughton |
| 5,962,285 A | 10/1999 | Anderson |
| 8,241,879 B2 | 8/2012 | Picataggio |
| 8,609,874 B2 | 12/2013 | Woods |
| 8,729,298 B2 | 5/2014 | Zang et al. |
| 8,778,658 B2 | 7/2014 | Picataggio |
| 2009/0162892 A1 | 6/2009 | Pompejus |
| 2013/0096343 A1 | 4/2013 | Tietz |
| 2013/0217081 A1 | 8/2013 | Pearlman |

*Primary Examiner* — Deborah D Carr
(74) *Attorney, Agent, or Firm* — Richard P. Silverman & Assoc., LLC (57) ABSTRACT

Disclosed is a process for the separation and purification of a diacid from a fermentation broth withdrawn directly from a fermentation zone for producing the diacid, wherein the fermentation broth comprises the diacid and water, a corresponding monoacid, and a corresponding ω-hydroxyacid. The process comprises passing the fermentation broth to a filtration zone having a filtration media and filtering the fermentation broth to provide a filtered feedstock. The filtered feedstock and a desorbent stream are passed to a simulated moving bed separation zone (SMB) operating in reverse phase at effective SMB conditions. The diacid may be adipic, acid, a 6-carbon atom diacid, or dodecanedioic acid, a 12-carbon atom diacid. The process is useful in simplifying the manufacturing the manufacture of diacids produced by fermentation. Adipic acid is used as monomer for the production of nylon. Dodecanedioic acid is used in antiseptics, coatings, painting materials, corrosion inhibitors, surfactants, and engineering plastics.

15 Claims, 4 Drawing Sheets

SEPARATION OF ADIPIC ACID AND DODECANEDIOIC ACID FROM CORRESPONDING MONOACID AND HYDROXY ACID

FIELD OF THE INVENTION

The invention relates to a method for separating diacids such as adipic and dodecanedioic acids as purified acids from fermentation broths containing these diacids and their corresponding monoacid and ω-hydroxyacid. More particularly, the invention relates to a simulated moving bed process (SMB) for the separation and isolation of adipic acid and dodecanedioic acid from fermentation broths. Adipic acid can used as monomer for the production of nylon by a polycondensation reaction with hexamethylene diamine to produce 6,6-nylon. Other major applications also involve polymers: it is a monomer for production of polyurethane and its esters may be used as plasticizers. Dodecanedioic acid is a dicarboxylic acid used in antiseptics, coatings, painting materials, corrosion inhibitors, surfactants, and engineering plastics.

BACKGROUND

Adipic acid (AA) is an organic compound with the formula $(CH_2)_4(COOH)_2$. Adipic acid has the following structure:

Adipic acid is a white crystalline solid used primarily in the manufacture of nylon-6,6 polyamide. Thus, from an industrial perspective, adipic acid is the most commercially important dicarboxylic acid.

Dodecanedioic acid (DDDA) is a dicarboxylic acid which is primarily used in the manufacture or preparation of antiseptics, coatings, painting materials, corrosion inhibitors, surfactants, and engineering plastics.

Dodecanedioic acid (DDDA) is used in the production of high performance nylon 6,12, molding resins, as well as adhesives and powder coatings.

Conventional adipic acid process involves the conversion of cyclohexane to adipic acid using a two-step oxidation process in nitric acid. The process requires exotic metallurgy for handling hot nitric acid (titanium). In addition, the conventional process produces significant quantities of by-product succinic acid and glutaric acid which require energy intensive separation steps, particularly crystallization. Because the succinic acid crystallizes at a temperature slightly above adipic acid, and glutaric acid crystallizes at a temperature slightly below adipic acid, there is a very narrow window of concentration and temperature wherein adipic acid can be crystallized without also crystallizing the succinic and glutaric acids. Commercially, this separation requires conducting the crystallization at sub-ambient temperatures at high vacuum, in order to remove water from the crystallizer solution as the crystals are precipitating out of solution. The vacuum compression requirement is both highly capital intensive, and highly energy intensive.

In 2012, U.S. Pat. No. 8,241,879 discloses engineered microorganisms that produce six-carbon organic molecules such as adipic acid, methods for manufacturing such microorganisms and methods for using them to produce adipic acid and other six-carbon organic molecules. More particularly, U.S. Pat. No. 8,241,879 discloses a process for a biological method for preparing adipic acid using a genetically modified yeast to convert glucose, and/or a paraffin (e.g., plant or petroleum based, such as hexane or coconut oil) to adipic acid via fermentation. U.S. Pat. No. 8,778,658, discloses and improved process for preparing adipic acid by fermentation from palm oil fatty acid.

The production of adipic acid and other diacids, such as dodecanedioic acid, by fermentation provides a new route to theses valuable materials and further avoids the production or coproduction of succinic and glutaric acids which essentially eliminates the difficult separation and purification requirements of the conventional production methods which rely on expensive crystallization. The new biological fermentation methods provide an aqueous fermentation broth comprising the diacids and their corresponding monoacid and ω-hydroxyacid. Typically, the diacids are present in the fermentation broth in concentrations of about 10 weight percent.

Such advances in the production of adipic acid produce fermentation broths which require new separation and purification solutions to produce diacids such as adipic and dodecanedioic acids as purified acids from fermentation broths containing these diacids and their corresponding monoacid and ω-hydroxyacid.

Simulation of a moving sorbent bed is described in U.S. Pat. No. 2,985,589 (Broughton et al.). In accomplishing this simulation, it is necessary to connect a feed stream to a series of beds in sequence, first to bed no. 1, then to bed no. 2, and so forth for numerous beds, the number of beds often being between 12 and 24. These beds may be considered to be portions of a single large bed whose movement is simulated. Each time the feed stream destination is changed, it is also necessary to change the destinations (or origins) of at least three other streams, which may be streams entering the beds, such as the feed stream, or leaving the beds. The moving bed simulation may be imply described as dividing the bed into series of fixed beds and moving the points of introducing and withdrawing liquid streams past the series of fixed beds instead of moving the beds past the introduction and withdrawal points. A rotary valve used in the Broughton process may be described as accomplishing the simultaneous interconnection of two separate groups of conduits.

Examples of simulated moving bed processes are disclosed, for instance, in U.S. Pat. No. 6,379,554 (method of displacement chromatography); U.S. Pat. No. 5,102,553 (time variable simulated moving bed process), U.S. Pat. No. 6,093,326 (single train, sequential simulated moving bed process); and U.S. Pat. No. 6,187,204 (same), each of the contents of the entirety of which is incorporated herein by this reference.

Methods are sought to recover target diacids components, such as adipic acid and dodecanedioic acid from fermentation broths resulting from biological methods for preparing diacids from fatty acids.

SUMMARY

The process of the present invention relates to the purification of diacids such as adipic or dodecanedioic acid from fermentation broths. Applicant has discovered a separation process for the recovery of essentially pure diacid directly from a fermentation broth for the production of either 6-carbon atom diacid (AA) or 12-carbon atom diacid (DDDA). Applicant's process can be carried out at essentially the same temperature conditions as the fermentation reaction. Applicant's process is based on reversed phase simulated moving bed separation (SMB) and using a selective stationary phase adsorbent and an effective mobile phase desorbent extracts minor components, minimizes opportunity for esterification of the product, and provides a diacid product which on a solvent free basis is essentially free of the corresponding monoacid and ω-hydroxyacid. By being essentially free of the corresponding monoacid and ω-hydroxyacid, the diacid product comprises or contains greater than or equal to 99 wt-% diacid and less than or equal to 1 wt-% of the corresponding monoacid and ω-hydroxyacid.

In one embodiment, the invention is a process for the separation and purification of a diacid from a fermentation broth withdrawn directly from a fermentation zone for producing the diacid, wherein the fermentation broth comprises the diacid and water, a corresponding monoacid, and a corresponding ω-hydroxyacid. The process comprises passing the fermentation broth to a filtration zone having a filtration media and filtering the fermentation broth to provide a filtered feedstock. The filtered feedstock and a desorbent stream are passed to a simulated moving bed separation zone (SMB) operating in reverse phase at effective SMB conditions. The SMB zone comprises a plurality of adsorbent beds. Each adsorbent bed contains a hydrophobic stationary phase agent which is a bonded silica gel having a surface with bonded hydrocarbon groups selected from the group consisting of C1, C2, C4, C8 and C18. The SMB zone provides a raffinate stream comprising a diacid, water, and desorbent, and an extract stream comprising the desorbent, water the corresponding monoacid, and the corresponding ω-hydroxyacid. The raffinate stream is essentially free of the corresponding monoacid and the corresponding hydroxyacid. The raffinate stream is passed to a raffinate desorbent recovery zone to recover a high purity diacid stream and a first recovered solvent stream. The extract stream is passed to an extract desorbent recovery zone to recover a byproduct stream comprising the corresponding monoacid and the corresponding ω-hydroxyacid, and provide a second recovered desorbent stream. At least a portion of the first and second recovered desorbent streams are returned to the SMB zone to provide at least a portion of the desorbent stream. At least a portion of the byproduct stream is returned to the fermentation zone.

DETAILED DESCRIPTION OF THE INVENTION

In the production of diacids using a biological fermentation route, an intermediate product is produced which must be removed or maintained at a low concentration in the purified product acid. For example, the fermentation route to adipic acid (AA) starts with using hexanoic acid (HA) or caproic acid (CA) as the feedstock. Bacterial fermentation oxidizes CA to hydroxy-caproic acid (HCA) which is further oxidized to adipic acid (AA). Fermentation broth effluent contains the main product AA along with unreacted CA and HCA. CA and HCA have to be separated from AA so they can be recycled to the bacterial fermentation zone, and a pure AA is produced. Similar situation exists with fermentation of lauric acid (LA) to dodecanoic acid (DDDA) wherein the intermediate is 12-Hydroxydodecaneoic acid (HDDA).

Efficient separation and isolation of pure diacids from fermentation broths containing up to 10 wt % of the diacid and 0.5 wt % of the corresponding fatty acid (monoacid) or ω-hydroxyacid is a critical requirement for the use of the target diacid product.

The fermentation broth derived from the bioreactor will typically contain or comprise a 90:5:5 ratio by weight of diacids to monoacid to hydroxyacid. The following Table 1, shows the typical composition of the 6 and 12 carbon atom target products in the fermentation broth. Isolation of at least 95 percent of the diacids with a purity of greater than or equal to 99 weight percent is desired.

TABLE 1

Typical Fermentation Broth Composition by Carbon Number of Acid

|  |  | Percent by Weight |
|---|---|---|
| 6-Carbon Atom Diacid | Adipic Acid |  |
|  | Solvent | 89 |
|  | Adipic Acid | 10 |
|  | Hexanoic Acid | 0.5 |
|  | 6-Hydroxycaproic Acid | 0.5 |
| 12-Carbon Atom Diacid | Dodecanedioic Acid |  |
|  | Solvent | 89 |
|  | DDDA | 10 |
|  | Lauric Acid | 0.5 |
|  | 6-Hydroxydodecaneoic Acid | 0.5 |

Applicant evaluated various types of sorbents and desorbents for use in the separation process. Applicant discovered a unique combination of stationary and mobile phase material which can provide a continuous simulated moving bed chromatographic separation (SMB) process to directly produce the purified diacid from the crude fermentation broths of both the 6 carbon and the twelve carbon atom diacids without requiring the pretreatment of the crude fermentation broths prior to the SMB separation.

Stationary Phase

The stationary phase adsorbent for use in the reverse phase SMB zone of the present invention is a hydrophobic stationary phase agent which is a bonded silica gel having a surface with bonded hydrocarbon groups selected from the group consisting of C1, C2, C4, C8 and C18. More particularly, the hydrophobic stationary phase agent is a bonded silica gel such as C8 silica gel or C18 silica gel. It was found that reverse phase hydrophobic adsorbents such as C8 and C18 provided significant selectivities for separating diacids from their corresponding monoacid and ω-hydroxyacid components than hydrophobic adsorbents. It was discovered that silica and alumina sorbents did not show any significant retention of the compounds of interest. Batch chromatographic separation showed the ability of the C18 adsorbent to perform the enrichment of the diacid component while significantly reducing the concentration of the corresponding monoacid and ω-hydroxyacid components in the extract stream by using a polar solvent as the loading solvent and a polar solvent as the desorbent solvent. Preferably the stationary phase adsorbent is a C8 or C18 adsorbent having a particle diameter of between about 300 and about 500 microns, a porosity of at least 60 Angstroms and a carbon loading of at least 10% w/w (weight percent).

Mobile Phase Desorbent

The mobile phase desorbent of the present invention for use in the reverse phase SMB zone when the stationary phase is a hydrophobic adsorbent is a polar solvent such as alcohol. Methanol provided the best performance in combination with the hydrophobic adsorbent as the stationary phase. Preferably the mobile phase desorbent comprises methanol or methanol and water. Preferably, the mobile phase desorbent is a mixture of methanol and water having a ratio of methanol:water of from 1 part methanol:99 parts water to 99 parts methanol:1 part water. Most preferably, the mobile phase desorbent is a mixture of methanol and water having a ratio of methanol:water of from 5 parts methanol:95 parts water to 95 parts methanol:5 parts water. Most preferably, the mobile phase desorbent is a mixture of methanol and water having a ratio of methanol:water of 5 parts methanol to 95 parts water. It was discovered that methanol or ethanol in any variation in methanol:water ratio, or in any ethanol:water ratio did not show any significant retention of the compounds of interest.

Feed Preparation

In the present invention, it was discovered that the fermentation broth could be processed directly in a simulated moving bed system as an SMB feedstock following a filtration step. Preferably, the filtration step was carried out as an ultrafiltration with a filter having a filter size equal to or less than 5 microns. More preferably, the filtration step was carried out as an ultrafiltration with a filter having a filter size equal to or less than 1 micron. The SMB will operate in a reversed phase, wherein the enriched product is recovered in a raffinate stream and the impurities, or in this case, the intermediates are recovered in an extract stream. Preferably, on a dry basis the diacid (adipic acid or dodecanedioic acid) in the fermentation broth comprises from about 2 wt-% to about 15 wt-% of components in the fermentation broth. More preferably, the SMB feedstock comprises from about 5 wt-% to about 10 wt-% of diacids in the fermentation broth. Most preferably, the SMB feedstock comprises from about 10 wt-% components in a solvent.

Operating Conditions

The filtration or ultrafiltration step and the SMB process are advantageously carried out at the temperature and pressure which are equal to or substantially the same as the fermentation reaction. Preferably, the filtration step and the SMB process are carried out at about atmospheric pressure and at a temperature ranging from about 15 to about 40° C. More preferably, the filtration step and the SMB process are carried out at about atmospheric pressure and at a temperature ranging from about 15 to about 40° C. Most preferably, the filtration step and the SMB process are carried out at about atmospheric pressure and at a temperature of about 37° C. The operation of the SMB system is carried out at a constant temperature within a plurality of adsorbent beds. The SMB feed stream, or feedstock, is introduced and components are adsorbed and separated from each other within the adsorbent beds. A separate liquid, the mobile phase desorbent, is used to counter currently displace the feed components from the pores of the stationary phase adsorbent. During the SMB cycle of the present invention, adsorbent beds are advanced through a desorption zone, a rectification zone, an adsorption zone, and a regeneration zone. The description of the SMB cycle as a 2-3-2-1 cycle means that in the cycle, 2 adsorbent beds are in the rectification zone, 3 adsorbent beds are in the rectification zone, and 2 adsorbent beds are in the adsorption zone, and 1 bed is idle.

Applicant's process provides a continuous process for the production of high purity diacid at high purity; i.e., where the purity of the diacids (adipic acid or dodecanedioic) is essentially free of corresponding monoacid and ω-hydroxyacid or wherein the concentration of the diacid on a solvent free basis comprises or contains the diacid in a concentration which is greater than or equal to about 99 wt-%. More preferably, applicant's process provides a continuous process for the production of diacid having a purity of greater than or equal to about 99.5 wt-%, and most preferably, applicant's process provides a continuous process for the production of diacid having a purity of greater than or equal to about 99.8 wt-%.

DETAILED DESCRIPTION OF THE DRAWINGS

Figure 1:
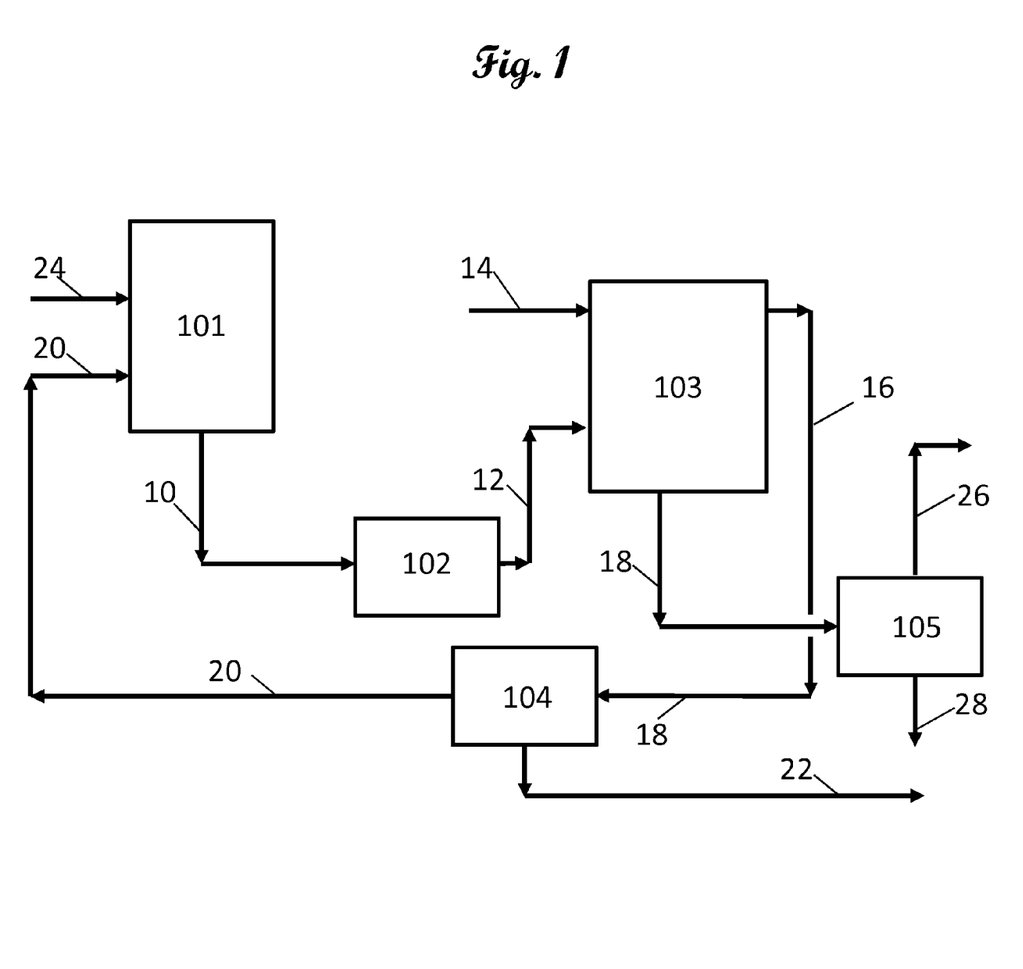
FIG. 1 is a schematic process flow diagram illustrating one embodiment of one embodiment of the invention.

The process of the present invention in one embodiment is illustrated in FIG. 1. According to FIG. 1, a fermentation broth in line 10 is withdrawn from fermentation zone 101. The fermentation zone comprises a biological reactor for preparing a diacids such as adipic acid or dodecanedioic acid by fermentation such as described in U.S. Pat. No. 8,778,658. The fermentation comprises the diacids and corresponding monoacid and ω-hydroxyacid components. The fermentation broth in line 10 is passed to a filtration zone 102 containing a filter media having a filter size of less than or equal to 5 microns. More preferably, the filter media in filtration zone 102 has a filter size of less than or equal to 1 micron. A filtered feedstock is withdrawn from the filtration zone 102 in line 12 and passed directly to a simulated moving bed separation zone (SMB) 103. The filtered feedstock in line 12 and a desorbent stream in line 14 are introduced to the simulated moving bed separation zone (SMB) 103. The SMB zone 103 comprises a plurality of adsorbent beds, for example 8 adsorbent beds or more and containing a stationary phase agent which is selective for the adsorption of the corresponding monoacid and ω-hydroxyacid components. The SMB zone 103 is operated in reversed phase SMB operation in a manner which provides a raffinate stream comprising the product diacid in line 18, and an extract stream in line 16 comprising the corresponding monoacid and ω-hydroxyacid components. The SMB is operated in an effective SMB cycle to provide the recovery of the diacid at recovery of greater than or equal to 90 weight percent based on the diacid in the feedstock. For example, the SMB zone can be operated in a 2-3-2-1 SMB cycle. The description of the SMB cycle as a 2-3-2-1 cycle means that in the cycle, 2 adsorbent beds are in the rectification zone, 3 adsorbent beds are in the rectification zone, and 2 adsorbent beds are in the adsorption zone, and 1 bed is idle. The extract stream in line 16 is passed to an extract solvent recovery zone 104 to provide a fermentation recycle stream in line 20 comprising the corresponding monoacid and ω-hydroxyacid components which are intermediates produced in the fermentation process and at least a portion of which can be returned to the fermentation reactor via line 20, and a recovered first solvent stream in line 22 comprising the desorbent. The process scheme described hereinabove will be the similar for the processing of a C6 carboxylic acid or a C12 carboxylic acid. The SMB stationary phase agent, or stationary phase adsorbent is a reverse phase hydrophilic adsorbent which is a bonded silica gel having a surface with bonded hydrocarbon groups selected from the group consisting of C1, C2, C4, C8 and C18. The desorbent employed in the SMB zone is methanol. The raffinate stream in line 18 comprises the diacid, water, methanol, and a minor amount of the monoacid and ω-hydroxyacid components. Preferably the extract stream comprises less than or equal to 0.5 wt % of monoacid and ω-hydroxyacid components based on the diacid in the extract stream. The raffinate stream in line 18 can be passed to a raffinate solvent recovery zone 105 to provide a diacid product stream in line 26 and a recovered second solvent stream in line 28. The at least a portion of the recovered first and second solvent streams in lines 22 and 28 may be recycled to provide a portion of the desorbent stream in line 14. The diacid product stream in line 26 may be passed to a finishing zone comprising distillation, evaporation, or drying to provide a finished diacid product.

Figure 2:
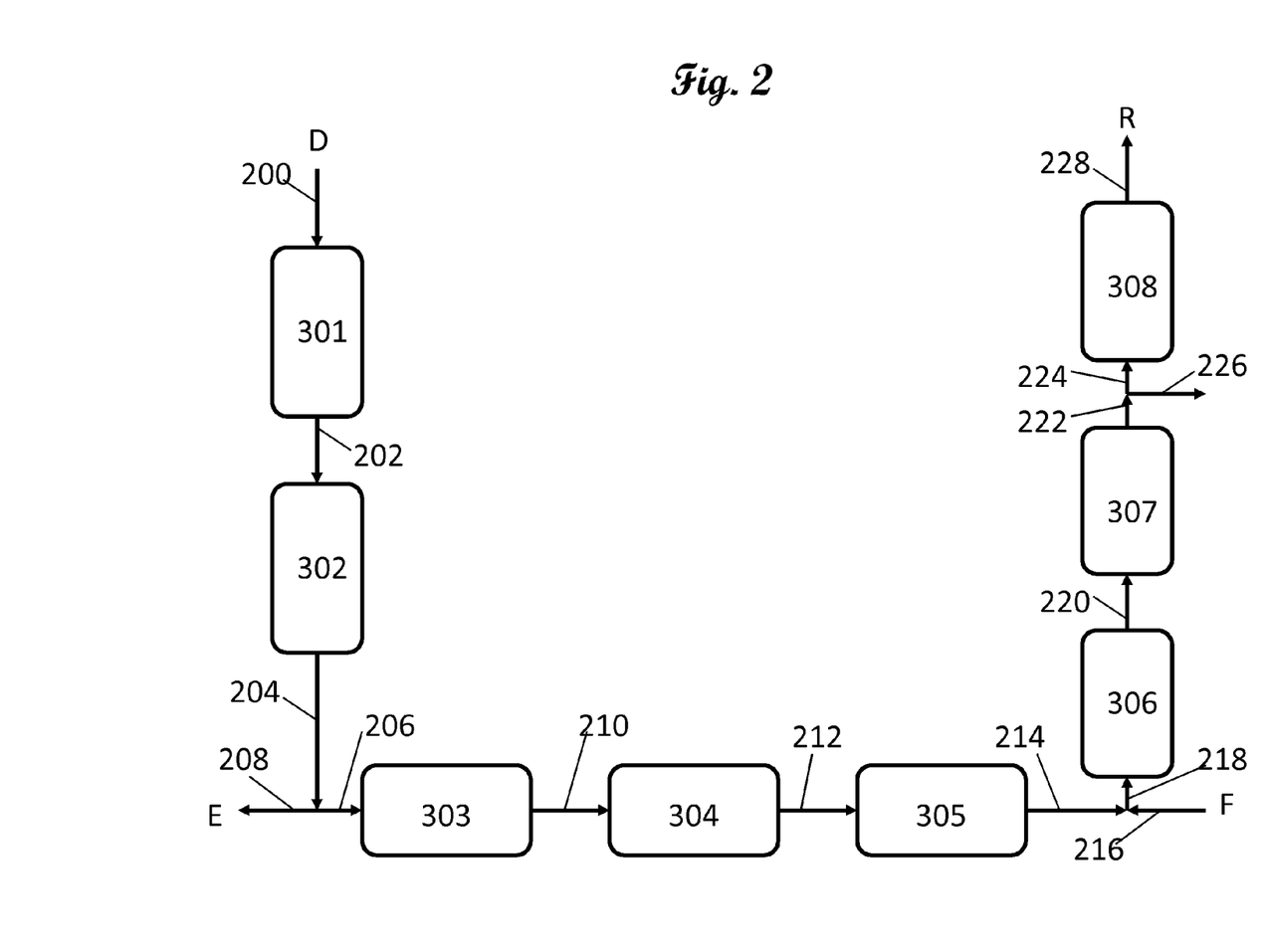
FIG. 2 is a schematic process flow diagram of a simulated moving bed process arrangement of one embodiment the invention.

Referring to FIG. 2, one embodiment of the simulated moving bed zone of the present invention as used in the SMB zone described hereinabove are shown herein as operating in a simulated moving bed (SMB) cycle based on an eight adsorbent bed arrangement. Adsorbent beds 301, 302, 303, 304, 305, 306, 307, and 308, containing a stationary phase adsorbent as described hereinabove, are disposed in a serial configuration such that in accordance with a prearranged cycle, conduit 202 provides fluid communication between the bottom of adsorbent bed 301 with the top of adsorbent bed 302, conduits 204 and 206 provide fluid communication between the bottom of adsorbent bed 302 and the top of adsorbent bed 303, conduit 210 provides fluid communication between the bottom of adsorbent bed 303 with the top of adsorbent bed 304, conduit 212 provides fluid communication between the bottom of adsorbent bed 304 with the top of adsorbent bed 305, conduits 214 and 218 provide fluid communication between the bottom of adsorbent bed 205 with the top of adsorbent bed 306, conduit 220 provides fluid communication between the bottom of adsorbent bed 306 with the top of adsorbent bed 307, conduits 222 and 224 provide fluid communication between the bottom of adsorbent bed 307 with the top of adsorbent bed 308, and conduit 226 provides for the withdrawal of fluid from the bottom of adsorbent bed 308 as the primary raffinate, and line 228 provides for the withdrawal of a secondary raffinate or void volume flush of the adsorbent bed 308 which is in transition from the desorption zone to the adsorption zone. According to the prearranged SMB cycle of the present invention, an SMB zone feed stream is passed to the SMB adsorption zone in line 216 and 218 to adsorbent bed 306. A primary raffinate stream is withdrawn from adsorbent bed 308 in conduits 222 and 226, and an extract stream is withdrawn via conduits 204 and 208 from adsorbent bed 302. A mobile phase desorbent stream as described hereinabove is introduced to adsorbent bed 301 in conduit 200. In this embodiment, the adsorbent beds 301-308 are indexed according to a 2-3-2-1 SMB cycle such that at least 2 adsorbent beds (301 and 302) undergo desorption in a desorption zone, at least 3 adsorbent beds (303, 304, and 305) undergo rectification in a rectification zone, and at least 3 adsorbent beds (306, 307, and 308) undergo adsorption in an adsorption zone during the SMB cycle of the present invention. The SMB zone employs a 2-3-2-1 SMB cycle.

It was discovered that using the C18 silica gel stationary phase adsorbent and a mobile phase desorbent comprising a methanol/water mixture of between about 100% methanol to a ratio of about 80 parts methanol to 20 parts water, the caproic acid was completely retained on the stationary phase adsorbent and separate absorbency peaks were achieved for the adipic acid (AA) and the 6-hydroxycaprioc acid (6HCA). It was discovered that using the C8 silica gel stationary phase adsorbent and a mobile phase desorbent comprising a methanol/water mixture of between about 100% methanol (0 parts water) to a ratio of about 80 parts methanol to 20 parts water as the mobile phase desorbent, the lauric acid was completely retained on the stationary phase adsorbent and separate absorbency peaks were achieved for the dodecanedioic acid (DDDA) and the 12-hydroxydodacaneoic acid (12HDDA).

Monoacids are more hydrophobic than hydroxy-monoacids which are more hydrophobic than diacids. It is believed that Caproic acid is strongly adsorbed on C18 silica gel, while HCA is less adsorbed, while AA is rejected. Selectivity between CA and AA is very high, while selectivity for adsorption of HCA with respect to AA is in the range of 2-3. Similar results were obtained for Lauric Acid, HDDA and DDDA on C8 silica gel.

The following examples are provided to illustrate the present invention. These examples are shown for illustrative purposes, and any invention embodied therein should not be limited thereto.

EXAMPLES

Example 1

Chromatic Separation

A test chromatographic column of 316 stainless steel and having an inside diameter of 10 mm and a length of 250 mm was prepared for liquid chromatography (LC) for use in establishing the elution profiles for the 6 and 12-carbon diacids, and their corresponding monoacid and ω-hydroxyacid, for each stationary phase agent tested. The passing of the feed is stopped and a desorbent elution is passed through the column and the eluate is collected for analysis. The chromatographic column was filled with about 12 gm of a bonded silica stationary phase sorbent (C18 SILICA GEL, C8 SILICA GEL) (Available from Orochem Technologies, Inc, Naperville, Ill.). The bonded silica particles were in the form of beads and were nominally 250-530 microns (μm) in diameter. The injection volume was about 5 ml. A flow of mobile phase desorbent as methanol at a rate of 0.5 ml/min was established in the column at a temperature of 60° C. The column was maintained at a temperature of 60° C. The feed solution was injected into the column and the eluent from the chromatographic column was monitored by refractive index using a Waters 410 RI detector (Available from Waters Corporation, Milford Mass.). The compositions were analyzed by mass spectrometry analysis. The feed solutions were as shown hereinbelow:

|  |  | Percent by Weight |
| --- | --- | --- |
| 6-Carbon Atom Diacid | Adipic Acid |  |
|  | Methanol (100%) | 89 |
|  | Adipic Acid | 10 |
|  | Hexanoic Acid | 0.5 |
|  | 6-Hydroxycaproic Acid | 0.5 |
| 12-Carbon Atom Diacid | Dodecanedioic Acid |  |
|  | Methanol(100%) | 89 |
|  | DDDA | 10 |
|  | Lauric Acid | 0.5 |
|  | 6-Hydroxydodecaneoic Acid | 0.5 |

Figure 3:
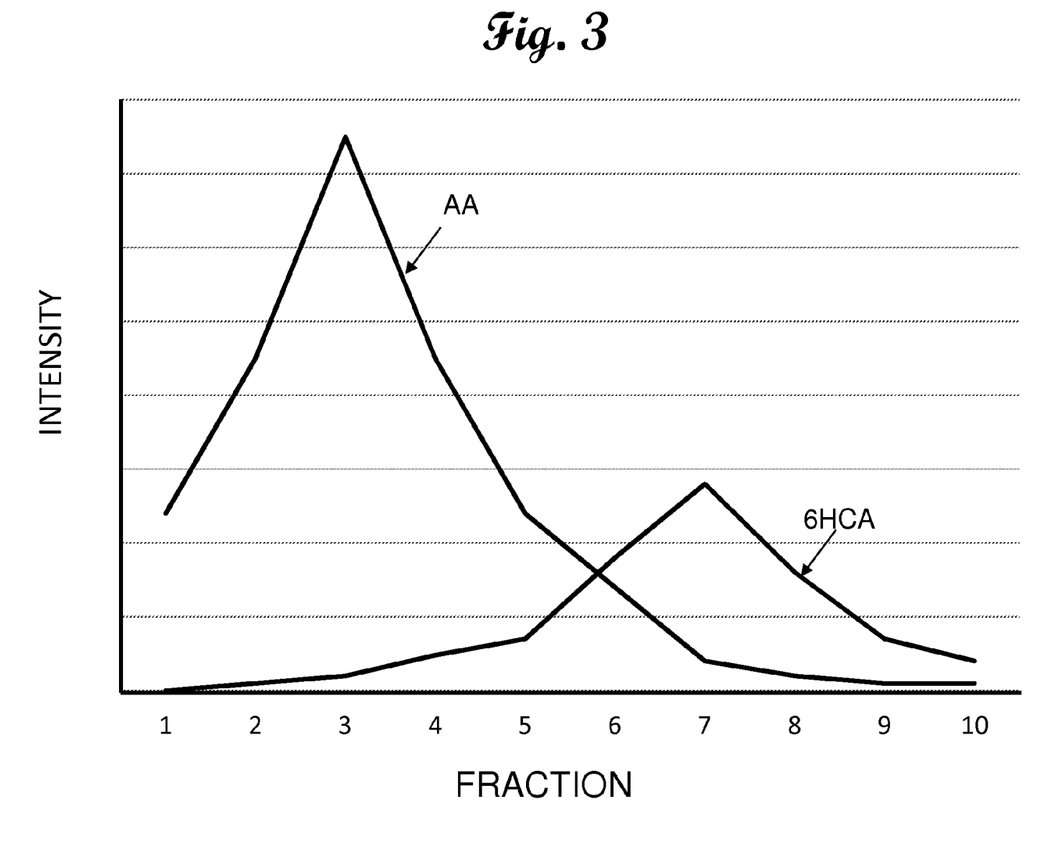
FIG. 3 shows the intensity of the adsorbent activity for the 6-carbon atom diacid mixture in a chromatic separation.

FIG. 3 shows the intensity of the adsorbent activity for the 6-carbon atom diacid mixture in methanol over a stationary phase consisting of C18 silica gel adsorbent. It was discovered that using the C18 silica gel stationary phase adsorbent and a mobile phase desorbent comprising a methanol/water mixture of between about 100% methanol to a ratio of about 80 parts methanol to 20 parts water, the caproic acid was completely retained on the stationary phase adsorbent and separate absorbency peaks were achieved for the adipic acid (AA) and the 6-hydroxycaprioc acid (6HCA). This demonstrates the feasibility of the SMB separation of the adipic acid from the fermentation broth.

Figure 4:
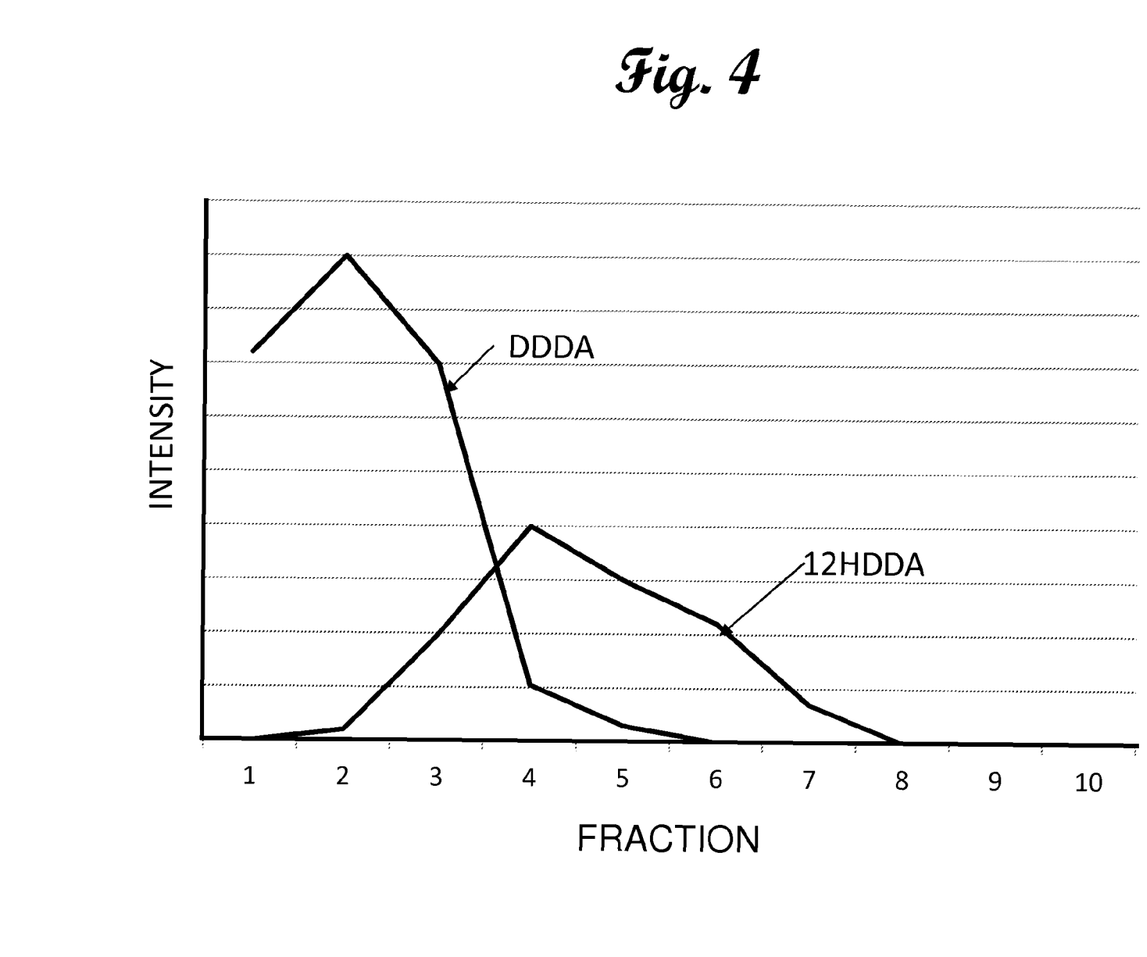
FIG. 4 shows the intensity of the adsorbent activity for the 12-carbon atom diacid mixture in a chromatic separation.

FIG. 4 shows the intensity of the adsorbent activity for the 12-carbon atom diacid mixture in methanol over a stationary phase consisting of C8 silica gel adsorbent. It was discovered that using the C8 silica gel stationary phase adsorbent and a mobile phase desorbent comprising a methanol/water mixture of between about 100% methanol to a ratio of about 80 parts methanol to 20 parts water as the mobile phase desorbent, the lauric acid was completely retained on the stationary phase adsorbent and separate absorbency peaks were achieved for the dodecanedioic acid (DDDA) and the 12-hydroxydodacaneoic acid (12HDDA). This demonstrates the feasibility of the SMB separation of the dodecanedioic acid from the fermentation broth.

The C18 silica gel adsorbent had a particle size of from 300-500 microns, about a 60 Angstrom pore size, a surface area of about 300 m$^2$/g and a carbon loading of about 22% w/w (weight percent). The C8 silica gel had a particle size of from 300-500 microns, about a 100 Angstrom pore size, a surface area of about 300 m$^2$/g and a carbon loading of about 18% w/w (weight percent).

Example 2

Overall Material Balance—Adipic Acid

An engineering material balance was developed from engineering principles and the chromatographic separation data for the processing of a fermentation broth withdrawn from a bacterial fermentation zone for the production of adipic acid. The fermentation was withdrawn from the fermentation zone at a pH of 4.5 and a temperature of 37° C. The aqueous fermentation broth has the following composition:

| Adipic Acid | 10 wt-% |
| --- | --- |
| Caproic Acid | 0.5 wt-% |
| 6-hydroxycaproicacid | 0.5 wt-% |
| Water | 89 wt-% |

The fermentation broth is filtered in a filtration zone having a 1 micron filtration media to provide a filtered feedstock for the SMB zone. The SMB zone used 100 percent methanol as the mobile phase desorbent and SMB operation was based on the C18 silica gel stationary phase agent. The SMB operation is carried out at a constant temperature of 37° C. and atmospheric pressure. Employing the above discussed 2-3-2-1 SMB cycle, the raffinate stream comprises the diacid product and essentially no caproic acid or hydroxyl caproic acid. On a dry or solvent free basis, the raffinate stream has the following composition:

| Component | Weight Percent |
| --- | --- |
| Adipic Acid | 99 |
| Caproic Acid | 0.2 |
| Hydroxycaproic Acid | 0.8 |
| Total | 100.0 |

The recovery of the adipic acid in the raffinate stream was about 95 weight percent and the purity of the adipic acid on a solvent free basis is greater than or equal to 99 weight percent. The concentration of the caproic acid and the hydroxy-caproic acid is less than 1 weight percent on a solvent free basis.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

We claim:

1. A process for the separation and purification of a diacid from a fermentation broth withdrawn directly from a fermentation zone for producing the diacid, said fermentation broth comprising the diacid and water, a corresponding monoacid, and a corresponding ω-hydroxyacid, said process comprising:

a. passing the fermentation broth to a filtration zone having a filtration media and filtering the fermentation broth to provide a filtered feedstock;

b. passing the filtered feedstock and a desorbent stream to a simulated moving bed separation zone (SMB) operating in reverse phase at effective SMB conditions, said SMB zone comprising a plurality of adsorbent beds, each adsorbent bed containing a reverse phase hydrophobic stationary phase agent being a bonded silica gel having a surface with bonded hydrocarbon groups selected from the group consisting of C1, C2, C4, C8 and C18 to provide a raffinate stream comprising a diacid, water, and desorbent, and an extract stream comprising the desorbent, water, the corresponding monoacid, and the corresponding ω-hydroxyacid, wherein the raffinate stream is essentially free of said corresponding monoacid and said corresponding hydroxyacid;

c. passing the raffinate stream to a raffinate desorbent recovery zone to recover a high purity diacid stream being essentially free of the corresponding monoacid, and the corresponding ω-hydroxyacid, and a first recovered solvent stream;
d. passing the extract stream to an extract desorbent recovery zone to recover a byproduct stream comprising said corresponding monoacid and said corresponding ω-hydroxyacid and a second recovered desorbent stream;
e. returning at least a portion of the first and second recovered desorbent streams to the SMB zone to provide at least a portion of the desorbent stream; and,
f. returning at least a portion of the byproduct stream to the fermentation zone.

2. The process of claim 1, wherein the hydrophobic stationary phase agent is a C18 bonded silica gel.

3. The process of claim 1, wherein the hydrophobic stationary phase agent is C8 bonded silica gel.

4. The process of claim 1, wherein the diacid is a 6-carbon atom diacid.

5. The process of claim 1, wherein the diacid is a 12-carbon diacid.

6. The process of claim 1, wherein the diacid is adipic acid, the corresponding monoacid is caproic acid, and the corresponding w-hydroxyacid is 6-hydroxycaproic acid.

7. The process of claim 1, wherein the diacid is dodecanedioic acid, the corresponding mono acid is lauric acid, and the corresponding ω-hydroxyacid is 12-hydroxydodecanedioic acid.

8. The process of claim 1, further comprising passing the high purity diacid stream to a finishing zone to provide a pelletized, granulated, or flaked diacid product.

9. The process of claim 1, wherein the effective conditions include an SMB temperature ranging from about 15 to about 40° C.

10. The process of claim 1, wherein the fermented broth comprises about 10 wt-% diacid and less than or equal to about 0.5 of each of the corresponding mono acid and the corresponding ω-hydroxyacid.

11. The process of claim 1, wherein the raffinate stream being essentially free of the corresponding monoacid, and the corresponding ω-hydroxyacid has a purity of greater than or equal to about 99 wt-% of the diacid on a solvent free basis.

12. The process of claim 1, wherein the desorbent stream comprises methanol or a mixture of methanol and water.

13. The process of claim 1 wherein the desorbent stream comprises from 80 parts methanol to 20 parts water to 100 parts methanol to 0 parts water.

14. The process of claim 1, wherein the reverse phase hydrophobic stationary phase agent comprises a C18 bonded silica gel having a particle size of about 300-500 microns, a pore size of about 60 Angstrom, a surface area of about 300 m2/g, and a carbon loading of about 22% w/w.

15. The process of claim 1, wherein the reverse phase hydrophobic stationary phase agent comprises a C8 bonded silica gel having a particle size of about 300-500 microns, a pore size of about 100 Angstrom, a surface area of about 300 m2/g, and a carbon loading of about 18% w/w.

* * * * *